United States Patent [19]
Davis

[11] Patent Number: 5,595,187
[45] Date of Patent: Jan. 21, 1997

[54] ANALYTICAL SPECIMEN CUP SYSTEM AND METHOD

[75] Inventor: Richard C. Davis, Palm Harbor, Fla.

[73] Assignee: Urocath Corporation, Tampa, Fla.

[21] Appl. No.: 262,535

[22] Filed: Jun. 20, 1994

[51] Int. Cl.⁶ ..................................................... A61B 5/00
[52] U.S. Cl. .......................... 128/771; 128/760; 604/403
[58] Field of Search ....................................... 128/760, 771; 604/317, 318, 403, 408, 409

[56] References Cited

U.S. PATENT DOCUMENTS

| | | |
|---|---|---|
| 3,774,455 | 11/1973 | Seidler et al. . |
| 3,924,741 | 12/1975 | Kachur et al. . |
| 4,024,952 | 5/1977 | Leitz . |
| 4,109,530 | 8/1978 | Kim . |
| 4,769,215 | 9/1988 | Ehrenkranz .......................... 128/771 X |
| 4,827,944 | 5/1989 | Nugent . |
| 4,832,046 | 5/1989 | Parrish .................................. 128/771 |
| 5,069,878 | 12/1991 | Ehrenkranz .......................... 128/771 X |
| 5,119,830 | 6/1992 | Davis . |
| 5,211,182 | 5/1993 | Deutsch et al. ......................... 128/771 |
| 5,380,289 | 1/1995 | Hemstreet et al. ................... 128/771 X |
| 5,429,804 | 7/1995 | Sayles .................................. 128/771 X |

*Primary Examiner*—Sam Rimell
*Attorney, Agent, or Firm*—Griffin, Butler, Whisenhunt & Kurtossy

[57] ABSTRACT

An analytical specimen cup system (10) includes a lid (14) comprising outer and inner partitions (42, 40) for defining a test space (44) having a chemical test strip (30) mounted therein. The inner partition defines a raised test-strip shelf (61) on which the chemical test strip is mounted, a sump (64) with a floor (62) positioned substantially below the raised shelf, and an opening-defining member (48) for defining an opening (50) to allow test fluid to be transferred from an analytical specimen cup (12) to the test space. A mouth (60) of the opening is vertically positioned intermediate the raised test-strip shelf and the sump floor. In one embodiment the analytical specimen cup has a membrane (24) covering its mouth (18) and is sterilized separate from the lid. The inner partition includes a specimen-release device (52) for uncovering the opening of the opening-defining member as well as for piercing the membrane.

14 Claims, 1 Drawing Sheet

ANALYTICAL SPECIMEN CUP SYSTEM AND METHOD

BACKGROUND OF THE INVENTION

This invention relates generally to specimen cups, chemical test strips for analyzing contents of analytical specimen cups and, specifically, to analytical specimen cups which are combined with chemical test strips.

It has been suggested to combine chemical test strips with analytical specimen cups so that contents of the specimen cups can be analyzed without the necessity of opening the specimen cups and inserting chemical strips therein. For example, U.S. Pat. No. 4,827,944 to Nugent discloses a body fluid sample collection tube having a number of bores therein for allowing a sample in the tube to impregnate adjacent dry chemistry patches. A plastic film wrap is pre-shrunk over the tube and the patches so as not to allow specimen fluids to escape beyond the patches. When a specimen is introduced into the collection tube of this invention a portion of the specimen passes immediately through the bores and impregnates, simultaneously and immediately, the plurality of patches so that an analysis of the fluid specimen can be made immediately. The specimen remains thereafter in continuous contact with the patches. One difficulty with this system is that it is usually not desirable to immediately test collected body fluids when they are first placed in a specimen cup. In this regard, most chemical patches, pads or test strips are time sensitive and do not, therefore, retain appropriate test colors over even short periods of time. Similarly, if the specimen remains in continuous contact with the patches so that the patches are not exposed to air, the patches may not properly react so that their colors do not reliably change as required. Thus, a technician observing the patches cannot obtain an accurate reading therefrom.

U.S. Pat. No. 5,119,830 to Davis describes an analytical specimen cup coupled with a test strip which overcomes some of the disadvantages of Nugent (U.S. Pat. No. 4,827,944). That is, the analytical specimen cup of U.S. Pat. No. 5,119,830 to Davis has a lid with outer and inner partitions to define a test space therebetween in which a chemical test strip is mounted. A fluid specimen in a cup is selectively introduced to the chemical test strip by manipulating a frangible valve which brakes an opening in the inner partition. Thus, the analytical specimen cup described in U.S. Pat. No. 5,119,830 to Davis allows technicians to control when fluid specimen is introduced to a chemical test strip so that the technicians need only do this when they are prepared to read and record the data.

Although the device in the Davis U.S. Pat. No. 5,119,830 overcomes to some extent the "time sensitive" problem of the Nugent system it does not completely overcome the "continuous contact" problem which prevents the patches from being exposed to air. That is, once the specimen is introduced to the test strip it remains substantially in continuous contact therewith. Thus, once a technician has introduced the specimen to the test strip it may be difficult for him to properly read the test strip and/or properly record the data therefrom. Thus, it is an object of this invention, to provide an analytical specimen cup system and method which allows one to immediately take accurate data therefrom without undue difficulty.

Another difficulty, common to both Nugent (U.S. Pat. No. 4,827,944) and Davis (U.S. Pat. No. 5,119,830), is that it is difficult to sterilize their analytical specimen cups and test strips. In this regard, it is sometimes necessary that specimen cups be sterilized so that there is no bacteria therein which could affect the specimen over a longer period of time. However, most normal sterilizing methods adversely affect chemical test strips and patches. That is, if chemical test strips are sterilized along with specimen cups, the test strips no longer provide accurate analyses of specimens contained in the specimen cups. Unfortunately, both Nugent (U.S. Pat. No. 4,827,944) and Davis (U.S. Pat. No. 5,119,830) require that the test strips thereof be sterilized along with the specimen cups. Therefore, it is an object of this invention, to provide an analytical specimen cup system and method which allows a specimen cup to be sterilized while not requiring that a test strip thereof to be sterilized.

A related difficulty with the devices of both Nugent (U.S. Pat. No. 4,827,944) and Davis (U.S. Pat. No. 5,119,830) is that if their chemical test strips remain unsterilized, they automatically contaminate entire specimens placed in their cups. This is because portions of liquid specimens contacting the chemical strips thereof are allowed to then flow freely back to the specimens remaining in the specimen cups thereof. Thus, it is an object of this invention to provide an analytical cup system and method which can be used for introducing and partitioning a portion of a specimen from a specimen cup to a test strip thereof without unduly contaminating a main portion of the liquid specimen remaining in the specimen cup.

Presently, dry chemical test strips are still usually introduced into urine or other fluidic specimens by dipping them therein and then exposing them to air. Such a procedure definitely contaminates a fluid specimen, and thereby adversely affects further tests run with the fluid specimen (such as using the fluid specimen with a culture). Such chemical test strips provide visual indications of quantitative properties of a specimen fluid such as: pH, protein, glucose, ketone, bilirubin, blood, urobilinogen, and many other fluid sample components. Changes in color of the chemical test strips are indicative of these characteristics of fluid specimens and therefore provide technicians with information as to what if any further testing may be required. When a fluid specimen and test strip are combined a technician must read the colors of the various patches of the test strip, analyze these colors, and record them on a chart. During this process, a number of mental and physical steps are required which, if not carried out accurately, can lead to the recording of false data which can, in turn, lead to serious, if not fatal, problems. Thus, it is an object of this invention to provide an analytical specimen cup system and method of its use which reduces the number of physical and mental steps required of technicians in reading and recording data.

SUMMARY

According to principles of this invention a lid of an analytical specimen cup system has outer and inner partitions defining a test space in which a chemical test strip is mounted with the inner partition defining: a raised test-strip holder on which the chemical test strip is mounted, a lower sump having a floor position substantially below the raised test-strip holder for receiving and retaining test fluid which drains downwardly from the raised test-strip holder, and an opening-defining member for selectively defining an opening for allowing test fluid to be transferred from a cup interior space into the test space but not allowing it to return to the cup interior space. In one embodiment the opening-defining member defines an upper mouth of the opening positioned vertically intermediate the raised test-strip holder and the sump floor. An analytical specimen cup for this system can be fitted with a membrane across a top thereof so that the cup can be separately sterilized. The lid includes a specimen release device for selectively piercing the membrane when the lid is on the specimen cup.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENTS

Figure 2:
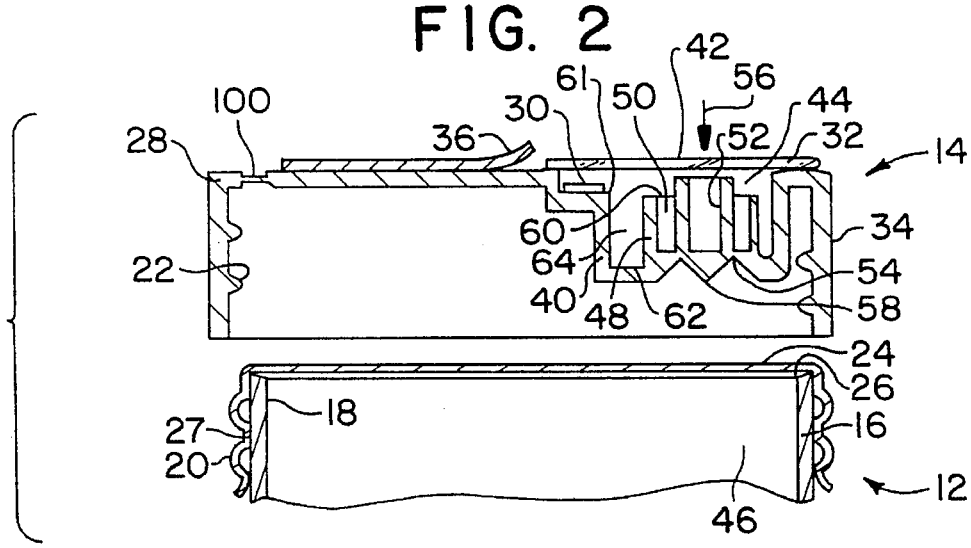
FIG. 2 is a fragmented exploded view of the system of FIG. 1 taken on line II—II in FIG. 1 with a peel-off label being partially removed for illustrative purposes.

An analytical specimen cup system 10 of this invention comprises a specimen cup 12 and a specimen-cup lid 14. Looking at FIG. 2, the specimen cup, or base container, 12 has a wall 16 for defining a container mouth 18. The container mouth 18 is surrounded by external ribs or threads 20 which mesh with internal grooves or threads 22 of the lid 14. The container mouth 18 of the specimen cup 12 is covered by a thin membrane 24, such as a plastic or metallic membrane, which is sealably adhered to an end 26 and an outer surface 27 of the wall 16 so as to stretch across the container mouth 18 and seal the specimen cup 12 against contamination. In this regard, the specimen cup 12, with its membrane 24, can be sterilized separately from the lid 14, with the membrane 24 ensuring that a cup interior space 25 of the specimen cup 12 remains sterilized, at least until the membrane 24 is pierced.

Looking now in more detail at the lid 14, the lid 14 comprises a lid main member 28 with a dry chemical test strip 30 and a thin transparent sheet of plastic 32 adhered thereto. Such a plastic film may be comprised of a single adhesive material, such as mylar, or may be of other materials, polyethylene, laminates or other subbstances which may be adhered, glued, heat-sealed, R-F sealed or otherwise sealably connected to the surface of the main member 28. As mentioned above, the lid main member 28 has the internal grooves or threads 22 on an inner surface of a skirt 34 thereof. The lid 14 also includes a pressure-sensitive-peel-off-label color-analysis chart 36 which is adhered to the lid main member 28 beside or over the thin sheet of plastic 32 and the test strip 30. In this regard, a portion of the lid main member 28 forms an inner partition 40 while the thin sheet of plastic 32 forms an outer partition 42; with the inner and outer partitions 40 and 42 defining a test space 44 therebetween. The test strip 30 is positioned in the test space 44. As can be seen in the drawings, the test space 44 is separated from the cup interior space 25 of the specimen cup 12 on which the lid is mounted by the inner partition 40. As mentioned above, the outer partition 42 is transparent for allowing the user to see into the test space 44.

The inner partition 40 includes a tubularly-shaped, snorkel-like, opening-defining member 48 for defining an opening 50 for allowing test fluid to be transferred from the cup interior space 25 into the test space 44. Positioned in the opening 50 is a specimen release device 52 which is molded as one piece with the inner partition 40, which is, in turn, integral with the lid main member 28. In this regard, the specimen release device 52 is attached to the rest of the inner partition 40 at a circular frangible connection 54 which can be broken by downward pressure, in a direction of an arrow 56 on the top of the specimen release device 52. The specimen release device 52 has at a bottom end thereof one or more sharp teeth 58 which can cut into the membrane 24 extending across the container mouth 18 when the specimen release device 52 is pressed downwardly.

The opening-defining member 48 defines an upper mouth 60 of the opening 50 which is vertically positioned intermediate a raised shelf 61 on which the test strip 30 is mounted and a floor 62 of a sump 64 surrounding the opening-defining member 48. In other words, the opening mouth 60 is slightly below the raised shelf 61 and well above the floor 62 of the sump 64.

Figure 1:
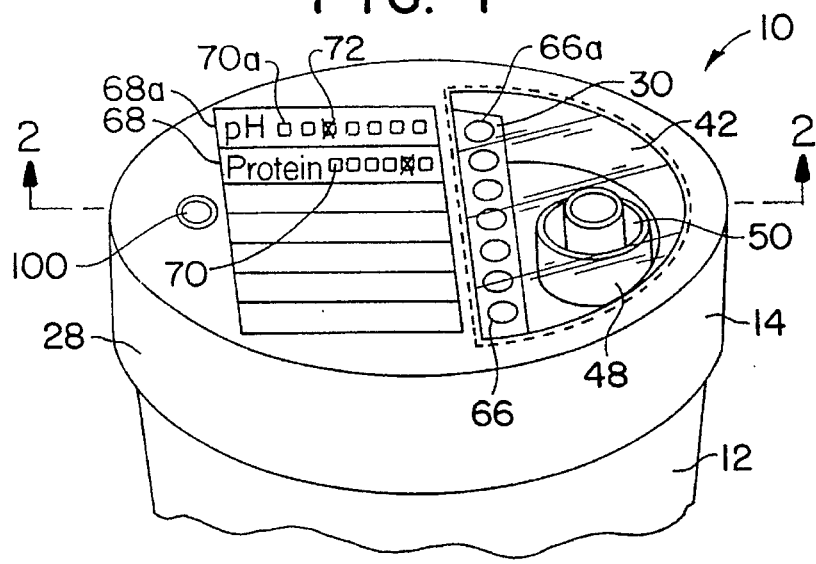
FIG. 1 is a schematic isometric view of an analytical specimen cup system of this invention.

As can be seen in FIG. 1, the test strip 30 comprises a line of chemical patches 66, each of which changes to a degree of color indicative of a characteristic of the test fluid. In this regard, for example, one of the patches will change to a particular color, or shade of color, depending upon a pH level of the test fluid when it is contacted by the test fluid. The peel-off color-analysis chart 36 has lines 68 of color blocks 70 thereon, each line corresponding to one of the chemical patches 66. For example, as is indicated in FIG. 1, there is a line 68a of color blocks 70a for the chemical patch 66a on which a technician can indicate the pH level of test fluid in the specimen cup 12. Each of the color blocks 70a in a line 68 has a color which is representative of a possible color that its respective chemical patch 66 can attain when it is contacted by the test fluid. A technician places a cross 72 on the color block 70 most closely representing the color of its associated chemical patch 66. The same is repeated for each line 68 of color blocks 70 for each of the chemical patches 66 to respectively indicate the pH level, protein, ketone, etc. The peel-off color-analysis chart can then be peeled off and placed into a permanent record to document the test.

Figure 3:
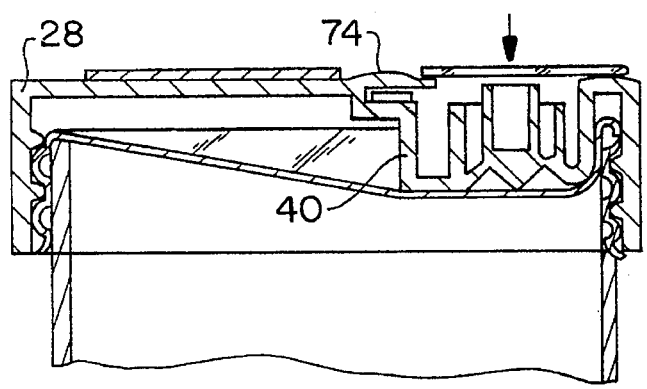
FIG. 3 is a view similar to FIG. 2, but with the lid not being exploded from the specimen cup, rather being mounted thereon, and with the lid having a slightly modified structure of an embellished embodiment.

Looking now at overall operation of the analytical specimen cup system 10, the lid 14 is manufactured separately from the specimen cup 12 and its membrane 24 so that the specimen cup 12 can be sterilized using standard methods of sterilization and covered, either before or after the sterilization, by the membrane 24 which protects the sterilization. The lid 14, by contrast, is manufactured in a "clean" environment and is not sterilized so that its test strip 30 is not affected by the sterilization process and therefore can provide accurate readings. A specimen cup system 10 can be stored and transported as a unit with the lid 14 mounted on the specimen cup 12 in such a manner that the membrane 24 protecting the sterilized specimen cup 12 is not broken thereby, as depicted in FIG. 3, until such an operation is desired. Alternately the lid is attached to the cup 12 then both are sterilized together, with the test strip 30, plastic 32, and label being applied afterwards in a "clean" environment.

When a technician desires to place a specimen in the analytical specimen cup system 10 he separates the lid 14 from the specimen cup 12 and forcefully pulls the membrane 24 from the container mouth 18 of the specimen cup 12. The specimen is then placed in the cup interior space 25. The membrane 24 is then again placed tightly over the container mouth 18 so as to ensure that no outside bacteria are introduced into the cup interior space 25 and the lid 14 is secured tightly onto the container mouth 18, thereby stretching the membrane 24, but not piercing it.

As is often the case, the technician (which would include a doctor, nurse, or the like) who collects the test fluid specimen is not the same technician who will analyze the specimen. Thus, there may be a period of time which elapses between the collection of the specimen and its analysis.

When a technician wishes to analyze the specimen test fluid he depresses the top end of the specimen release device 52 by flexing the thin sheet of plastic 32 in a direction of the arrow 56 and thereby breaks the frangible connection 54 and also causes the sharp tooth 58 at the lower end of the specimen release device 52 to cut into the membrane 24. This clears the opening, or passage 50 so that test fluid can now be transferred from the cup interior space 25 into the test space 44. The analyzing technician then turns the analytical specimen cup system 10 upside down so that test fluid of the specimen will pass through the opening 50 into the test space 44. Gravity causes the test fluid to flow through the opening mouth 60 and come into contact with the test strip 30. However, a surface of the test fluid in the test space 44 will not rise above the opening mouth 60 of the opening-defining member 48 because surrounding pressure will not allow it to do so. Thus, the test fluid in the test space 44 is limited so that the test fluid does not completely fill the test space 44. However, in any case, sufficient test fluid enters the test space to contact the test strip 30 on the raised shelf 61. Once the test fluid has stopped flowing from the cup interior space 25 to the test space 44 the technician again inverts the analytical specimen cup system 10 to a right-side-up position. When the technician does this, virtually all of the test fluid which has entered the test space 44 drains into the sump 64. That is, this test fluid which entered the test space 44 is drained from the raised shelf and the test strip 30; however, it is not allowed to fall back into the cup interior space 25. Thus, the test strip 30 is exposed to air so that it can properly react to the specimen, changing colors to indicate characteristics of the specimen. At the same time, the fluid which has flowed into the test space 44 of the clean but unsterilized lid 14 is not allowed to contaminate the fluid specimen remaining in the cup interior space 25.

The technician then appropriately marks the peel-off color-analysis chart 36 according to the colors of the patches on the test strip 30 and removes the peel-off color-analysis chart 36 from the analytical specimen cup system 10 and places it on the patient's chart.

It will be appreciated by those of ordinary skill in the art that the analytical specimen cup system of this invention and the method of its use allow the specimen cup 12 to be sterilized and to remain sealed until it is used.

A further benefit of the system and method of this invention is that it ensures that the test strip does not remain in continuous contact with the test fluid for a long period of time after the test fluid is introduced to the test strip. By providing a sump within the test space and by limiting the amount of test fluid which can enter the test space the test fluid can be drained from the test strip into the sump. Thus, it is assured that the test strip is exposed to the oxygen in air immediately after it has been exposed to the specimen.

By providing a peel-off color-analysis chart adjacent the test strip the number of physical and mental steps which a technician must go through in order to analyze and record the test fluid is reduced. That is, by providing an analysis chart immediately adjacent to a test strip, the technician can easily compare the two. Similarly, by not then requiring the technician to transcribe information to a permanent record, the amount of work required of the technician, and the associated chance of mistake, is reduced.

While the invention has been particularly shown and described with reference to a preferred embodiment, it will be understood by those of ordinary skill in the art that various changes in form and detail may be made therein without departing from the spirit and scope of the invention.

FIG. 3 depicts, for example, an embellishment of this invention in which a portion of the lid main member 28 is integrally formed as an optical magnifying lens 74 for making it easier for a technician to read the patches of the test strip. In this regard, it would also be possible in this case to cover the membrane 24 with opaque material, or simply make it of opaque material. Thus, only the test strip 30 would then be visible in the test space 44.

In one embodiment there is a thin circular sampling zone 100 created in the lids main member 28 which allows piercing by a needle which can be inserted into the fluid sample in the cup interior space 25 for withdrawing fluid in a sterile manner, without unduly exposing the fluid specimen. The hole created by the needle passing through this sampling zone 100 is small enough that fluid cannot easily escape therethrough, thereby preventing contamination of and from the laboratory surroundings after the sampling zone 100 is punctured.

It is obvious to those of ordinary skill in the art that the sump 64 could have various configurations as could the opening-defining member 48. Further, it is not essential that the raised shelf have the exact configuration depicted in FIGS. 2 and 3. In this regard, in one embodiment the raised shelf is at an angle to the horizontal so as to achieve better drainage.

In one embodiment the specimen release device 52 is adherently connected to the plastic 32 to prevent its loss into the cup interior space 25 upon puncturing the frangible zone 50.

In one embodiment the membrane 44 is omitted, where it is not necessary that the analytical specimen cup system be sterile (such as in a doctor's office where the system will be immediately disposed of after its use).

Similarly, in another embodiment the specimen release device 52 is not sealingly connected to the rest of the lid, but rather is simply slidably connected thereto for piercing the membrane. Also, the specimen release device 52 could be simple valve.

Also, the lens 74 could be manufactured separately of a different material and snapped or adhered into place.

Similarly, the sampling zone 100 could be made of a latex or other elastomeric material which would totally seal after needle withdrawal.

While this invention specifically relates to medical fluid sample testing, and more specifically urine testing, it is obvious to those skilled in the art that chemical testing of other fluid samples, i. e. river waters, air, pool water, oceanic sediments, etc., can be just as easily effected by this system.

The embodiments of the invention in which an exclusive property or privilege are claimed are defined as follows:

1. A method of analyzing a specimen comprising the steps of:

preparing a lid for an analytical specimen cup to have an enclosed test space with a test strip mounted therein and preparing a cup therefor separately with a temporary cover for covering the mouth of the specimen cup;

sterilizing the specimen cup with its temporary cover;

removing the temporary cover and placing a fluid specimen in the specimen cup;

attaching the lid to the mouth of the specimen cup;

inverting the specimen cup to cause the fluid specimen to flow through an opening in the lid into the test space and thereby activate said test strip.

2. A method for analyzing a specimen in a specimen cup comprising the steps of:

providing a lid for the specimen cup, said lid including an outer partition and an inner partition for defining a test space separated from a cup interior space of said specimen cup when said lid is mounted on said specimen cup, said outer partition being transparent for allowing a user to see into said test space and said inner partition having an opening for allowing test fluid to be transferred from said cup interior space into said test space;

providing a chemical test strip mounted in said test space on a raised test strip holder of the inner partition;

forming the inner partition to define a lower sump having a sump floor positioned substantially below said raised test strip holder and said opening when said specimen cup is in an upright position for receiving and retaining test fluid which drains downwardly from said raised test-strip holder;

inverting the specimen cup to an upside down position to cause the fluid specimen to flow through the opening in the lid into the test space and thereby activate said test strip but not fill said test space; and reinverting said specimen cup to an upright position for thereby allowing said fluid specimen to drain from said chemical test strip into said sump.

3. A method as in claim 2 wherein is further including the steps of providing a peel-off color-analysis chart on said lid, marking said peel-off color-analysis chart according to colors of the chemical test strip and removing the peel-off color-analysis chart and placing it on another document.

4. A method of assembling an analytical specimen cup system comprising the steps of:

providing a specimen cup for defining a cup interior space and a cup mouth;

placing a lid on said specimen cup so as to close the mouth thereof, said lid having an inner partition for partially defining a test space separated from the cup interior space of the specimen cup on which the lid is mounted;

sterilizing the analytical specimen cup and the lid mounted thereon together;

thereafter applying a chemical test strip to the lid inside the test space;

thereafter applying a film to said lid to form an outer partition of said test space so as to inclose said chemical strip in said test space.

5. A method as in claim 4 wherein is included the further step of applying a peel-off-label color chart to said lid outside of test space adjacent the chemical test strip.

6. An analytical specimen cup system comprising:

a specimen cup;

a lid for the specimen cup, said lid including an outer partition and an inner partition for defining a test space separated from a cup interior space of the specimen cup on which the lid is to be mounted, said outer partition being transparent for allowing a user to see into said test space and said inner partition having an opening for allowing test fluid to be transferred from said cup interior space into said test space, said interior partition having a raised test-strip area and a lower sump floor positioned substantially below said raised test-strip area and said opening when said specimen cup is in an upright position for receiving and retaining test fluid which drains downwardly from said raised test-strip area, said inner partition having a fluid passage opening for communicating the test space with the interior space of the analytical specimen cup;

a chemical strip mounted in said test space on said raised test-strip area of the inner partition;

whereby a fluid specimen can be placed in the interior space of the analytical specimen cup, the analytical specimen cup, with the lid thereon, can be inverted to an up-side-down position to cause the fluid specimen to flow through the passage opening in the inner partition into the test space and thereby activate the test strip, and said specimen cup with said lid can be reinverted to an upright position for thereby allowing said fluid specimen to drain from said chemical test strip onto said lower sump floor.

7. A method of assembling and using an analytical specimen cup system comprising the steps of:

providing a specimen cup for defining a cup interior space and a cup mouth;

applying a color chart to an exterior surface of said analytical specimen cup system said color chart including colors corresponding to colors a chemical test strip brought into contact with said specimen achieves to indicate presence of substances in said specimen, whereby a technician can compare the colors of the color chart with the colors of the chemical test strip for reading the chemical test strip, wherein said color chart is formed as a removable label attached to the exterior surface of said analytical specimen cup system but which can be easily removed therefrom and attached to another surface;

wherein are further included the steps of:

placing a specimen in said cup interior space;

causing a chemical strip to be brought into contact with said specimen;

marking those colors of said color chart which correspond to the colors achieved by said chemical test strip; and after said colors of said color chart have been marked, removing said color chart from said specimen cup system and attaching it to a record for documenting the presence of substances in said specimen.

8. A method as in claim 7 wherein are further included the steps of:

providing on said specimen cup system inner and outer partitions for defining a test space separated from the cup interior space of the specimen cup, with said outer partition comprising a transparent film for allowing a user to see into said test space from outside said analytical specimen cup system and said inner partition including a means for allowing said specimen to pass from said interior space into said test space;

applying a chemical test strip to the inner partition inside the test space, said chemical test strip being of a type which changes colors to indicate presence of substances with which it comes into contact.

9. A method as in claim 8 wherein are further included the steps of:

placing a specimen in said cup interior space;

causing said specimen to flow from said interior space into said test space through said means for allowing said specimen to pass from said interior space into said test space; and marking those colors of said color chart which correspond to the colors achieved by said chemical test strip.

10. A method as in claim 7 wherein said color chart applied to said exterior surface is formed as a peel-off label adhering to the exterior surface of said analytical specimen cup system but which can be easily removed therefrom and adhered to another surface.

11. A method as in claim 10 wherein is further included the step of, after said colors of said color chart have been marked, peeling said color chart from said specimen cup system and adhering it to a record for documenting the presence of substances in said specimen.

12. An analytical specimen cup system having an exterior surface, said cup system comprising:

a specimen cup for defining a cup interior space for holding a specimen and a cup mouth;

a chemical test strip for being brought into contact with said specimen to be held in said cup and for changing colors to indicate presence of substances in said specimen a color chart on said exterior surface of said analytical specimen cup system, said color chart including colors corresponding to colors the chemical test strip achieves to indicate presence of substances, said color chart being a removable label which is attached to the exterior surface of said analytical specimen cup system by a means for removable attachment for allowing said color chart to be easily removed therefrom and attached to a record for documenting the presence of substances in said specimen.

13. An analytical specimen cup as in claim 12 wherein said specimen cup system includes both inner and outer partitions for defining a test space separated from the cup interior space of the specimen cup, said outer partition comprising a transparent film for allowing a user to see into said test space from outside said specimen cup system and said inner partition including a means for allowing said specimen to pass from said interior space into said test space;

wherein said chemical test strip is adhered to a wall inside the test space so that it can be observed through said transparent film of said outer partition while the colors of said color chart are marked.

14. An analytical specimen cup system as in claim 12 wherein said color chart applied to said exterior surface is formed as a peel-off label which adheres to the exterior surface of said analytical specimen cup system but which can be easily removed therefrom and adhered to another surface.

* * * * *